United States Patent

Soe et al.

[11] Patent Number: 5,821,068
[45] Date of Patent: Oct. 13, 1998

[54] ANTI-HUMAN SOLUBLE FIBRIN ANTIBODY, HYBRIDOMA, AND IMMUNOASSAYING METHOD

[75] Inventors: Gilbu Soe; Isao Kohno; Kimiko Inuzuka; Yumiko Ito, all of Tokyo, Japan

[73] Assignee: Iatron Laboratories, Inc., Tokyo, Japan

[21] Appl. No.: 448,547

[22] PCT Filed: Nov. 1, 1994

[86] PCT No.: PCT/JP94/01844

§ 371 Date: Sep. 22, 1995

§ 102(e) Date: Sep. 22, 1995

[87] PCT Pub. No.: WO95/12617

PCT Pub. Date: May 11, 1995

[30] Foreign Application Priority Data

Nov. 2, 1993 [JP] Japan .................................. 5-297325

[51] Int. Cl.$^6$ ..................... G01N 33/543; G01N 33/577
[52] U.S. Cl. ..................... 435/7.21; 435/7.24; 435/7.94; 435/337; 436/518; 436/548; 530/388.25
[58] Field of Search .................. 435/7.21, 7.24, 435/7.94, 240.27, 337; 436/518, 548; 530/388.25

[56] References Cited

U.S. PATENT DOCUMENTS 5,099,004  3/1992  Nieuwehuizen ............... 530/387.9
5,441,869  8/1995  Dessauer et al. ............... 435/7.1
5,453,359  9/1995  Gargan et al. ................. 435/13

OTHER PUBLICATIONS

International Search Report for PCT/JP94/01844, Feb. 14, 1995.

W. Nieuwenhuizen et al. Thromb, Haemost., 68(3), 273–277, 1992.

U. Scheefers–Borchel et al., Proc. Natl. Acad. Sci., 82, 7091–7095, 1985.

W.J.G. Schielen et al, Pro. Natl. Acad. Sci., 86, 8951–8954, 1989.

*Primary Examiner*—David Saunders
*Attorney, Agent, or Firm*—Sughrue, Mion, Zinn, Macpeak & Seas, PLLC

[57] ABSTRACT

A monoclonal antibody that reacts with a human soluble fibrin but not with a human fibrinogen; a hybridoma that secretes the above antibody; and a method of assaying a human soluble fibrin with the above antibody. It is possible to determine the amount of soluble fibrin in the plasma of a patient specifically, readily and rapidly by agglutination and EIA without being affected by plasma fibrinogen, plasmin-degradation product of fibrinogen, fibrin fragment, and plasmin-degradation product of stabilized fibrin even without pretreating the plasma sample.

13 Claims, 4 Drawing Sheets

ANTI-HUMAN SOLUBLE FIBRIN ANTIBODY, HYBRIDOMA, AND IMMUNOASSAYING METHOD

This is a continuation application of PCT/JP94/01844, filed Nov. 1, 1994.

TECHNICAL FIELD

The present invention relates to a monoclonal antibody that reacts with a human soluble fibrin, but does not react with a human fibrinogen, a hybridoma that secretes the above monoclonal antibody, and a method of immunoassaying a soluble fibrin with the above monoclonal antibody. According to the immunoassay method of the present invention, it is possible to rapidly and accurately determine the content of soluble fibrin in the plasma sample without reacting with or affected by fibrinogen, various fibrinogen fragments, various fibrin fragments and various plasmin-degradation product of a stabilized fibrin present in the sample, even without pretreating the plasma sample with a protein-denaturing agent, such as sodium thiocyanate (KSCN), in a specific, reproducible and immunological manner. The term "human soluble fibrin" used herein means a fibrin-fibrinogen complex formed by binding fibrinogen with des AABB fibrin or des AA fibrin.

BACKGROUND ART

Thrombin acts on fibrinogen usually present in blood to consecutively release fibrinopeptide A from Aα chain and fibrinopeptide B from Bβ chain, and form fibrin monomer I (des AA fibrin) and fibrin monomer II (des AABB fibrin), respectively. The fibrin monomers can be present in blood up to a certain level as a soluble fibrin formed by binding with fibrinogen in blood. However, as the concentration of the fibrin monomers becomes high, the fibrin monomers are polymerized to produce a fibrin clot. Therefore, it is desirable to early detect the soluble fibrin in blood, for early prediction of the formation of the fibrin clot, i.e., the thrombus formation, to early effect the treatment for inhibiting blood coagulation, i.e., the thrombus formation. The detection of the soluble fibrin may be performed by an antibody that reacts with the soluble fibrin, but does not with fibrinogen.

For the above purpose, the preparation of antibodies specific to fibrin were reported. For example, Kudryk, et al. disclosed monoclonal antibodies which were derived using a fragment prepared by treating an amino terminus of fibrin with cyanogen bromide as an immunogen, and which reacted with an amino terminus of the fibrin β chain [Macromolecular Immunology, 89–94 (1984)]. Further, Hui, et al. discloses antibodies obtained by immunization with a peptide of the amino terminus of fibrin β chain [Hybridoma 5, 215–222 (1985)]. However, there was the disadvantage in that the antibodies only recognize the amino terminus of the fibrin β chain liberated from the fibrinopeptide B after the cleavage thereof, and thus cannot be used for the detection of the fibrin I, i.e., des AA fibrin.

European Patent Application No. 152,612 and Japanese Unexamined Patent Publication (Kokai) No. 60-158353 disclose an EIA method for determining fibrin, using an antibody derived from an animal immunized with an immunogen peptide from an α chain amino terminus newly produced by cleavage of fibrinopeptide A. However, the antibody cannot be reacted with a fibrin complex in blood, because the amino terminus of the fibrin α chain becomes masked after binding with fibrinogen or other fibrin which is present in blood in quantity. Therefore, to remedy said defect, it was necessary that the fibrin complex is pre-treated with a high concentration sodium thiocyanate in, and thereby converted to a fibrin monomer, before assaying [Blood Coagulation and Fibrinolysis, 4,97–102 (1993)]. Further, there existed the disadvantage in that the antibody reacts with plasmin-degradation products of fibrin, fibrin fragments X, Y, D and E, all of which have a same epitope.

WO 8,801,514 discloses a monoclonal antibody obtained by using a human fibrin as an immunogen. However, the antibody also reacts with fibrin fragments D, X and Y, and fibrinogen Aα chain, and thus, cannot be called an antibody specific for fibrin. Further, Japanese Unexamined Patent Publication (Kokai) No. 2-28197 (corresponding to Netherlands Patent Application No. 31,8801227) discloses a monoclonal antibody which reacts with a peptide of 111st to 207th amino acids of the amino acid sequence of the fibrinogen Aα chain. The monoclonal antibody does not react with fibrinogen, but specifically reacts with fibrin. In other words, the monoclonal antibody reacts both with fibrin I (des AA fibrin) and fibrin II (des AABB fibrin). However, the monoclonal antibody reacts also with D-dimer, Degata and fibrinogen Aα chain, and thus, cannot be called an antibody specific to fibrin. Further, it is not possible to exclude the influence of the plasmin-degradation products of fibrin, when an assaying system is made up using the above antibody.

DISCLOSURE OF INVENTION

The inventors of the present invention engaged in research to develop a method for simply and accurately measuring the soluble fibrin with good reproducibility, and as a result, discovered a monoclonal antibody which reacts with a neoantigen that is newly exposed in a fibrin molecule at the time when a fibrin-fibrinogen complex is formed by binding des AABB fibrin or des AA fibrin and the fibrinogen, but does not react with the human fibrinogen, and further found that if one of the above monoclonal antibodies or a combination of two of them is used, it is possible to rapidly, accurately and specifically determine the content of soluble fibrin in the plasma sample without affected by fibrinogen, various fibrinogen fragments x, Y, D or E, various fibrin fragments X, Y, D or E and various plasmin-degradation products of a stabilized fibrin present in the sample, even without pretreating the plasma sample with a protein-denaturing agent, such as potassium thiocyanate (KSCN). Therefore, the object of the present invention is to provide the above novel monoclonal antibodies, hybridomas that secrete the above monoclonal antibodies, and a method of immunological assaying using the above monoclonal antibody or antibodies.

The present invention relates to a monoclonal antibody which reacts with a human soluble fibrin, but does not react with a human fibrinogen.

The present invention also relates to a hybridoma that secretes the above monoclonal antibody.

Further, the present invention relates to a method of assaying a human soluble fibrin, characterized by bringing a sample into contact with the above monoclonal antibody immobilized on an insoluble carrier, and observing agglutination.

Furthermore, the present invention also relates to a method of immunological assaying a human soluble fibrin, characterized in that the above monoclonal antibody is immobilized on an insoluble carrier as a first antibody, bringing a sample into contact with said first antibody and then with a labeled second antibody which is an antibody of a same kind as or a different kind from the above antibody, and detecting a signal from said label of said second antibody bound with an immobilized first antibody-human soluble fibrin, or from said second antibody unbound the immobilized first antibody-human soluble fibrin.

Furthermore, the present invention also relates to a method for diagnosing disseminated intravascular coagulation (DIC), comprising the detection of a soluble fibrin in a biological sample by the above immunological assay.

BEST MODE FOR CARRYING OUT THE INVENTION

The present invention will be explained hereinafter in the order of the monoclonal antibodies, the hybridomas, and the immunological assay.

The monoclonal antibodies and hybridomas may be prepared, for example, using a human soluble fibrin as an immunogen. The human soluble fibrin used as an immunogen may be prepared in accordance with, for example, the method of Remo Largo, et al. [Blood, 47, 991–1002 (1976)]. More particularly, fibrinogen is dissolved in physiological saline. It is preferable that the saline contains an inhibitor (such as EDTA) to blood coagulation factors (in particular, factor XIII) which are coexisting in trace amounts in a standard reagent of fibrin. Then, thrombin is added to the fibrinogen solution, and the mixture is incubated at about 37° C. for about 90 minutes to form a fibrin clot. The fibrin clot is separated, washed and then dissolved in a urea solution. Insolubles are removed by, for example, centrifuging, to obtain purified fibrin monomers. The resulting purified urea-solubilized fibrin monomer may be used as an immunogen or a standard reagent in the immunoassay.

Alternatively, the fibrin clot formed by adding thrombin is dissolved in and dialyzed by an acetate buffer, such as 50 mM acetate buffer (pH 4.6), to prepare an acetate buffer-solubilized fibrin monomer which may be used as a standard reagent in the immunoassay.

Then, the immunogen solution of the purified urea-solubilized human fibrin monomer is used to immunize mammals (for example, mice, rats, rabbits, goats, and horses) by the in-vivo immunization method. More particularly, for example, the immunogen solution of the purified urea-solubilized human fibrin monomer is mixed with an equal volume of complete Freund's adjuvant or incomplete adjuvant until emulsified. The mixture is administered, for example, subcutaneously to mice (a first immunization). Then, the same procedure is repeated at intervals of two to four weeks for several immunizations. The spleens are removed aseptically several days after the final immunization, and crushed by a stainless steel mesh or the like to prepare the spleen cells which are used for the cell fusion.

As the other parent cells used for the cell fusion, that is, the myeloma cells, there may be used various types of known cell lines, such as, p3 (p3/×63-Ag8) [Nature, 256, 495–497 (1975), p3-U1 [Current Topics in Microbiology and Immunology, 81; 1–7 (1978)], NS-1 [Eur. J. Immunol., 6; 511–519 (1976)], MPC-11 [Cell, 8; 405–415 (1976)], SP2/0 [Nature, 276; 269–270 (1978)], FO [J. Immunol. Meth., 35; 1–21 (1980)], ×63.6.55.3 [J. Immunol., 123; 1548–1550 (1979)], S194 [J. Exp. Med., 148; 313–323 (1978)], R210 from rats [Nature, 277; 131–133 (1979)], or the like.

The cell fusion between the immunized spleen cells and myeloma cells may be carried out by ordinary methods. For example, a known fusion promoter (polyethylene glycol, Sendai virus, or the like) and optionally an auxiliary agent (dimethyl sulfoxide or the like) may be used. The ratio of the immunized spleen cells and myeloma cells may be the same as in ordinary methods. For example, spleen cells may be used in amounts about one to 10 times the amount of the myeloma cells. As the fusion medium, for example, the Dulbecco modified Eagle's medium (DMEM) containing 40% (w/v) polyethyleneglycol may be used. The fusion is carried out by thoroughly mixing the immunized spleen cells and myeloma cells in the above medium.

Then, a selecting medium (for example, HAT medium) is used to remove the cells other than the hybridoma. The target hybridomas are separated by detecting the presence of the antibodies produced in the supernatant of the hybridoma cultivation by, for example, the ELISA method. The resulting hybridomas of the present invention that secrete the desired monoclonal antibodies of the present invention can be successively cultured in ordinary media, and can be easily stored for long periods in liquid nitrogen or the like.

As the medium for cultivating the hybridomas, any medium suitable for cultivation of a hybridoma may be used. Preferably, a medium comprising the DMEM including fetal calf serum, L-glutamin, L-pyruvic acid and antibiotics (penicillin G and streptomycin) is used. The cultivation of the hybridoma is preferably carried out for example in a medium at a 5% $CO_2$ and 37° C. for about 3 days in the case of in vitro cultivation, or for about 14 days in the case of in vivo cultivation, for example, in the abdominal cavities of mice.

The target monoclonal antibodies of the present invention may be separated and purified from the cultivation liquid obtained by cultivating the hybridomas of the present invention by an ordinary method, or from the ascites of suitable mammals (for example, mice or rats) administered with the hybridomas of the present invention. When separating and purifying the monoclonal antibodies from the resulting cultivation liquid or mouse ascites, it is possible to use the method generally applied for the isolation and purification of proteins. As examples thereof, there may be mentioned the ammonium sulfate salting out, ion exchange chromatography, column chromatography using molecular sieve gel, affinity column chromatography using protein A binding polysaccharides, dialysis, lyophilization, or the like.

The resulting monoclonal antibodies of the present invention react with a human soluble fibrin, but do not react with a human fibrinogen. Further, the monoclonal antibodies of the present invention react with a neoantigen that is newly exposed in a fibrin molecule at the time when a human soluble fibrin, i.e., a fibrin-fibrinogen complex, is formed by binding des AABB fibrin or des AA fibrin and the fibrinogen, but do not react with a human fibrinogen.

The preferred monoclonal antibodies of the present invention are (1) the monoclonal antibody [hereinafter sometimes referred to the monoclonal antibody (1)], in particular, the monoclonal antibody FM No. 43-1 as mentioned in Examples as below, which specifically reacts with a urea-treated (i.e., urea-solubilized) des AABB fibrin, a urea-treated (i.e., urea-solubilized) plasmin-degradation product of a stabilized fibrin, and a urea-treated fibrin fragment (such as fragments X, Y and E), but does not react with a fibrinogen, a urea-treated plasmin-degradation product (such as fractions X, Y, D and E) of a fibrinogen, a urea-treated des AA fibrin nor a urea-treated des BB fibrin, and (2) the monoclonal antibody [hereinafter sometimes referred to the monoclonal antibody (2)], in particular, the monoclonal antibody FM No. 59-1 as mentioned in Examples as below, which specifically reacts with a urea-treated des AA fibrin, a urea-treated des AABB fibrin, a urea-treated plasmin-degradation product of a stabilized fibrin, and a urea-treated fibrin fragment (such as fragments X, Y and E), but does not react with a fibrinogen, a urea-treated plasmin-degradation product (such as fractions X, Y, D and E) of a fibrinogen, nor a des BB fibrin.

The term "urea-treated" used herein means that an antigen is generally dissolved in about 3 M urea solution.

Accordingly, the hybridomas of the present invention secretes the monoclonal antibodies which react with a human soluble fibrin, but do not react with a human fibrinogen, particularly, the monoclonal antibodies which react with a neoantigen that is newly exposed in a fibrin molecule at the time when a human soluble fibrin, i.e., a fibrin-fibrinogen complex, is formed by binding des AABB fibrin or des AA fibrin and the fibrinogen, but do not react with a human fibrinogen. Preferred hybridomas of the present invention secrete the monoclonal antibody (1) or (2).

It is possible to cause agglutination reaction only with a soluble fibrin without causing agglutination reactions with fibrinogen, plasmin-degradation products (such as fractions X, Y, D and E) of fibrinogen, fibrin fragments (such as X, Y, D and E), plasmin-degradation products of stabilized fibrin, and des BB fibrin in a sample, by immobilizing on an insoluble carrier at least one of the anti-soluble fibrin monoclonal antibodies, particularly the above monoclonal antibodies (1) and (2), and bringing the sample into contact with the monoclonal antibody or antibodies. Therefore, these antibodies are useful as a reagent for an immunological determination.

Further, it is possible to detect a signal only from a human soluble fibrin, but not from fibrinogen, plasmin-degradation products (such as fractions X, Y, D and E) of fibrinogen, fibrin fragments (such as X, Y, D and E), plasmin-degradation products of stabilized fibrin, and des BB fibrin in a sample, by immobilizing on an insoluble carrier at least one of the anti-soluble fibrin monoclonal antibodies, particularly the above monoclonal antibodies (1) and (2), as a first antibody, bringing a sample into contact with the immobilized first antibody, and then into contact with a labeled second antibody which is the anti-soluble fibrin monoclonal antibodies, particularly the above monoclonal antibodies (1) and (2), of a same kind as or a different kind from the first antibody. Therefore, the antibodies are useful as a reagent for an immunological determination.

Therefore, it is possible to carry out a method of immunoassay of the present invention, using the anti-soluble fibrin monoclonal antibodies of the present invention. The sample used in the immunoassay method of the present invention is not particularly limited, so long as it has a possibility to include the soluble fibrin. Examples thereof are physiological samples, in particular blood, serum, and plasma, or urine, in particular plasma. In the method of immunoassay method of the present invention, it is possible to avoid interference of the fibrinogen and the related substances present in the sample, even when the sample is directly used without pre-treatment.

In the method of the immunoassay according to the present invention using the agglutination reaction, any insoluble carrier generally used in the immunological determination methods using the agglutination reaction between antigens and antibodies, for example, latex particles (in particular, polystyrene latex particles) may be used. To immobilize the monoclonal antibodies of the present invention on the insoluble carrier, known methods, such as the chemical bonding method (using carbodiimide, glutalaldehyde, or the like as the cross-linking agent) or physical adsorption method may be used. Thus, a complex of the monoclonal antibody and the insoluble carrier may be produced and used for the immunoassay method of the present invention.

In the immunological determination method (agglutination reaction) of the present invention, one or two of the monoclonal antibodies immobilized on the above insoluble carrier are used. It is possible to use one or two types of antibody-carrier complexes prepared by immobilizing each of the monoclonal antibodies on an insoluble carrier, respectively, or to use a antibodies-carrier complex prepared by immobilizing two types of monoclonal antibodies on an insoluble carrier. Further, it is possible to use a combination of one type of antibody-carrier complex prepared by immobilizing one type of monoclonal antibody on an insoluble carrier and the other type of antibody-carrier complex prepared by immobilizing other type of monoclonal antibody on the other insoluble carrier. The agglutination reaction can be measured visually in the case of a slide plate, or spectroscopically using a specific wavelength in the case of a reaction cell, to determine the concentration of the soluble fibrin in the sample.

Specifically, in the immunological determination method (sandwich assay) of the present invention, the monoclonal antibody (1) or (2) is immobilized on an appropriate insoluble carrier to obtain an immobilized antibody. Then, the surface of the insoluble carrier is covered with an appropriate blocking agent, such as bovine serum albumin (BSA) or rabbit serum albumin (RSA), to avoid a non-specific bonding of the insoluble carrier and the sample. Thereafter, non-diluted sample is added to and contacted with the immobilized antibody for a certain period of time (for example, 5 minutes to 3 hours) at a certain temperature (for example, 4 to 40° C., preferably around room temperature) to cause a reaction (a primary reaction). Then, a second antibody which is a labeled monoclonal antibody (1) or (2) is added to and contacted with the mixture for a certain period of time (for example, 5 minutes to 3 hours) at a certain temperature (for example, 4 to 40° C., preferably around room temperature) to cause a reaction (a secondary reaction). The mixture is washed with an appropriate detergent, such as a physiological saline containing surfactant, and then, the amount of the labeled antibodies on the insoluble carrier is determined. It is possible to calculate the amount of the soluble fibrin in the sample from the value found. It is also possible to carry out the primary and secondary reactions at the same time.

The insoluble carrier which may be used in the sandwich method of the present invention is not particularly limited.

The examples of the carrier are a polymer material, such as polyethylene, polystyrene, polypropylene, polyvinyl chloride, polyester, polyacrylonitrile, fluororesin, cross-linked dextran or polysaccharide, or nitrocellulose, paper, agarose, or a combination thereof.

It is preferable to use an enzyme, fluorescent or phosphorescent substance as a label. It is possible to use alkaline phosphatase, peroxidase, β-D-galactosidase, as the enzyme; fluorescein isothiocyanate as the fluorescent substance; or acridinium ester or luciferin as the or phosphorescent substance.

As above, it is possible to diagnose disseminated intravascular coagulation (DIC) which is important in a clinical standpoint of view, or to accurately grasp progressing after treatment.

EXAMPLES

The present invention now will be further illustrated by, but is by no means limited to, the following examples.

Example 1

(a) Purification of Soluble Fibrin Monomer

The human soluble fibrin used as an immunogen may be prepared in accordance with, for example, the method of Remo Largo, et al. [Blood, 47, 991–1002 (1976)]. More particularly, 1 g (dry weight) of fibrinogen (Kabi) was dissolved in 2 liters of physiological saline containing 5% EDTA. Then, thrombin (50 NIH) was added and the mixture was incubated at 37° C. for 90 minutes. The resulting fibrin clot was washed with physiological salines (500 ml×3) by centrifugation. Then, the washed fibrin clot was dissolved in 20–50 ml of 5M urea solution. After the insolubles were removed by centrifugation, the concentration of the fibrin monomers was adjusted to 5 mg/ml, and the product [hereinafter sometimes referred to as the soluble fibrin monomer (U-FM)] was used as an immunogen or a standard reagent in the immunoassay.

Further, the fibrin clot formed by adding thrombin was dialyzed by a 50 mM acetate buffer (pH 3.5) to prepare an acetate buffer (pH 3.5)—solubilized fibrin monomer [hereinafter sometimes referred to as the soluble fibrin monomer (A-FM)], which was used for the same purpose.

(b) Preparation of Immunized Spleen Cells

The soluble fibrin monomer (A280 nm=0.1) was mixed with an equal volume of complete Freund's adjuvant until emulsified, and then, 200 µl of the mixture was administered intraperitoneally in BALB/c mice to immunize the same (first immunization). After 30 days, 200 µl of the above-mentioned mixture was administered intraperitoneally to the mice (second immunization). After 21 days from the second immunization, 200 µl of the diluted soluble fibrin solution prepared by diluting the soluble fibrin monomer (U-FM) immunogen solution (A 280 nm=0.1) with an equal volume of a physiological saline was administered intravenously to the mice (final immunization). After 3 days from the final immunization, the spleens were removed aseptically from the mice to use in the following cell fusion.

(c) Cell Fusion

The above-mentioned aseptically removed spleens were placed in a laboratory dish containing 5 ml of DME medium containing 15% fetal calf serum. Then, the spleens were perfused by about 15 ml of DME medium containing 15% fetal calf serum to flush out the spleen cells. The suspension of the spleen cells was passed through a nylon mesh. The spleen cells were collected in a 50 ml centrifugation tube and were centrifuged at 500×g for 10 minutes. To the resulting pellets, 4 ml of a hemolyzing solution (155 mM-$NH_4Cl$, 10 mM-$KHCO_3$, 1 mM-$Na_2EDTA$; pH 7.0) was added to suspend the pellets. The suspension was allowed to stand at 0° C. for 5 minutes to lyse the red blood cells therein. A DME medium containing 15% fetal calf serum was added, and the mixture was centrifuged. The resulting pellets were washed with a DME medium by the centrifugation method and the number of living spleen cells was counted.

The above spleen cells ($1\times10^8$) were added to about $2\times10^7$ precultivated mouse myeloma cells SP2/0-Ag14 (Rikagaku Kenkyusho Gene Bank), and the whole was thoroughly mixed in a DME medium, and centrifuged (500×g, 10 minutes). The supernatant was sucked up, and the pellets were thoroughly unfastened. 0.5 ml of 40% polyethylene glycol 4000 solution (warmed at 38° C.) was added dropwise, and then, the centrifugation tube was gently rotated by hand for 1 minute to thereby mix the polyethylene glycol solution with the cell pellets. Then, a DME medium warmed at 38° C. was added in 1 ml amounts every 30 seconds and the tube was gently rotated. After this procedure was repeated 10 times, 20 ml of a DME medium containing 15% fetal bovine serum was added and centrifugation was carried out (500×g, 10 minutes).

After the supernatant was removed, the cell pellets were washed twice by the centrifugation method with a HAT medium (prepared by adding, to a DME medium, aminopterin, thymidine and hypoxanthine so that the concentrations thereof become to $4\times10^{-7}$ M, $1.6\times10^{-5}$ M, and $1\times10^{-4}$ M, respectively) containing 15% fetal bovine serum, and then suspended in 40 ml of the HAT medium. The cell suspension was divided and poured into the wells of 96-well cell cultivation plates in an amount of 200 µl, and the cultivation was started in a carbon dioxide gas incubator containing 5% carbon dioxide gas at 37° C. During the cultivation, about 100 µl of the medium was removed from each of the wells at 2 to 3 day intervals and 100 µl of fresh HAT medium was added to select the hybridomas which grew in the HT medium. From the eighth day, the medium was substituted for a HAT medium (prepared by adding, to a DME medium, thymidine and hypoxanthine so that the concentrations thereof become to $1.6\times10^{-5}$ M and $1\times10^{-4}$ M, respectively) containing 15% fetal bovine serum and the hybridomas were observed. On the tenth day, the hybridomas producing the anti-soluble fibrin antibodies were screened by the ELISA method as mentioned below.

(d) Establishment of Hybridomas

The presence of produced antibodies in the supernatant of the hybridoma cultivation liquid was determined by the ELISA method. Into the wells of 96-well ELISA plates (Immulon; Nippon Dynatech K. K.), the soluble fibrin (U-FM) immunogen solution (A280 nm=0.05, diluted with physiological saline) was poured in an amount of 50 µl, respectively, and allowed to stand at 25° C. for 2 hours. Thereafter, the wells were washed three times with 0.05% Tween 20-physiological saline, then 50 µl of the supernatant of the cultivation liquid was added to the wells and a reaction was carried out at 25° C. for 1 hour.

Then, 50 µl of a peroxidase-conjugated anti-mouse antibody (Dako Co., Denmark) diluted 200-fold with Tween 20-physiological saline was added to the wells. After the reaction was completed, the wells were washed three times by 0.05% Tween 20-physiological saline. Thereafter, 250 µl of a solution containing 0.5 mM aminoantipyrine, 10 mM phenol, and 0.005% hydrogen peroxide was added to the wells, a reaction was carried out at 25° C. for 30 minutes, and the absorption at 490 nm of the wells was measured. As a result, antibody production was observed in three of the 192 wells. The hybridomas in the three wells were transferred to a 24-well plate and were cultivated for 4 to 5 days in a HT medium containing 15% fetal bovine serum. Thereafter, the presence of the produced anti-soluble fibrin antibodies was confirmed by the ELISA method, and then, cloning was carried out by the limiting dilution method. In the limiting dilution method, 100 µl of the cell suspension diluted with an HT medium so that the concentration of the hybridoma became 5 hybridomas/ml was poured into each of the wells of 96-well plate wherein $2\times10^4$ abdominal cells of normal BALB/C mice were poured in advance in each well. After 10 days, clones of the hybridoma producing anti-soluble fibrin specific antibodies were screened by the ELISA method.

As a result, 20 to 40 clones producing antibodies were obtained for each hybridoma. From these clones, stable ones exhibiting strong proliferation and a high ability for secreting antibodies were selected, and recloned by the same method as above, and two hybridomas FM No. 43-1 and FM No. 59-1 producing anti-soluble fibrin antibodies were obtained. The above hybridomas were domestically deposited in the National Institute of Bioscience and Human-Technology Agency of Industrial Science and Technology Agency of Industrial Science and Technology (Address: 1-3, Higashi 1-chome, Tsukuba-shi, Ibaraki-ken 305, Japan) on Oct. 27, 1993, and were transferred to international deposition on Oct. 27, 1994. The international deposition numbers (numbers in parenthesis [ ] following the international deposition numbers are domestic deposition numbers) are FERMBP-4846 [FERMP-13925] for the hybridoma FM No. 43-1, and FERMBP-4847 [FERMP013926] for the hybridoma FM No. 59-1. The reactivities of two monoclonal antibodies FM No. 43-1, and FM No. 59-1 secreted from the above two hybridomas with fibrinogen, fibrinogen fragments X, Y, D and E, fibrin fragments X, Y, D and E and plasmin-degradation products of stabilized fibrin were examined by the ELISA method as above, by covering the above antibodies on the 96-well ELISA plates. Hereinafter, the hybridoma FM No. 43-1 is called the hybridoma FM-1, the hybridoma FM No. 59-1 is called the hybridoma FM-2, the monoclonal antibody FM No. 43-1 is called the monoclonal antibody FM-1, the monoclonal antibody FM No. 59-1 is called the monoclonal antibody FM-2.

Example 2

Preparation of Monoclonal Antibodies (a) In Vitro Method

Mouse hybridoma FM-1 and FM-2 were cultivated respectively in DME media containing 15% fetal bovine serum at 37° C. for 72 to 96 hours in a 5% carbon dioxide atmosphere. After the cultures were centrifuged (10,000×g, 10 minutes), solid ammonium sulfate was gradually added to the supernatants so that a final concentration thereof was 50%. The mixtures were for 30 minutes while cooled with ice, then allowed to stand for 60 minutes and then centrifuged (10,000×g, 10 minutes). The residues were dissolved in a small amount of a 10 mM phosphate buffer (pH 8.0) and were applied to a column of DEAE-cellulose which had been equilibrated with a 1000-fold amount of 10 mM phosphate buffer. The monoclonal antibodies were eluted by the density gradient method from a 10 mM phosphate buffer (pH 8.0) to a 10 mM phosphate buffer (pH 8.0) containing 0.2M-NaCl. The eluted monoclonal antibodies were concentrated by the ultra filtration method and were dialyzed to a 0.1M phosphate buffer (pH 8.0). To remove the bovine serum IgG, the dialyzed products were passed through goat anti-bovine serum IgG-Sepharose 4B columns. Then, the passed solutions were filed to protein A-Sepharose 4B columns equilibrated with a 0.1M phosphate buffer (pH 8.0). The columns were eluted by a buffer (pH 3.5) to obtain the solution of the purified anti-FM specific monoclonal antibody FM-1 and similarly the monoclonal antibody FM-2.

(b) In Vivo Method

Pristane (2,6,10,14-tetramethylpentadecane) (0.5 ml) was administered intraperitoneally into 10 to 12 week old BALB/c mice. After 14 to 20 days, hybridoma FM-1 or FM-2 proliferated in vitro was inoculated into the abdominal cavities of the mice in an amount of $2\times10^6$ cells/mouse.

About 10 to 15 ml of ascites was obtained from a mouse for each of the hybridomas. The concentrations of the antibodies were 2 to 10 mg/ml. The purification of the monoclonal antibodies from ascites was carried out by the method same as that in vitro purification (however, except the step of passing through a column of goat anti-bovine serum IgG-Sepharose).

Example 3

Determination of Immunoalobulin Class and Specificity of Monoclonal Antibodies

The immunoglobulin class and specificity of the anti-FM specific monoclonal antibodies FM-1 and FM-2 were examined by the Ouchterlony immunodiffusion method, and the enzyme immunoassay method, respectively. The immunoglobulin class of the anti-FM specific monoclonal antibodies FM-1 and FM-2 was $IgG_2a$, respectively. The results are shown in Table 1.

TABLE 1

|  | Monoclonal antibody | |
|---|---|---|
| Antigen | FM-1 | FM-2 |
| Fibrinogen (a) | − | − |
| Fibrinogen (b) | − | − |
| Des AABB Fibrin monomer (a) | + | + |
| Des AABB Fibrin monomer (b) | − | − |
| Des AA Fibrin (a) | − | + |
| Des AA Fibrin (b) | − | − |
| Des BB Fibrin (a) | − | − |
| Des BB Fibrin (b) | − | − |
| Fibrinogen fragment X (a) (b) | − | − |
| Fibrinogen fragment Y (a) (b) | − | − |
| Fibrinogen fragment E (a) (b) | − | − |
| Dcate (a) (b) | − | − |
| Degta (a) (b) | − | − |
| Fibrin fragment X (a) | + | + |
| Fibrin fragment Y (a) | + | + |
| Fibrin fragment E1, E2 (a) | + | + |
| Fibrin fragment E3 (a) | + | + |
| Fibrin fragment X (b) | − | − |
| Fibrin fragment Y (b) | − | − |
| Fibrin fragment E1 E2 (b) | − | − |
| Fibrin fragment E3 (b) | − | − |
| D Dimer (a) (b) | − | − |
| DD/E (a) | + | + |
| DD/E (b) | − | − |
| Degradation products (mixture) of stabilized fibrin with plasmin (a) | + | + |
| Degradation products (mixture) of stabilized fibrin with plasmin (b) | − | − |
| Aα chain peptide 17–26 (GHRPLDKKRE)(SEQ ID NO: 1) | − | − |
| Bβ chain peptide 15–24 (GPRVVERHQS)(SEQ ID NO: 2) | − | − |

TABLE 1-continued

| | Monoclonal antibody | |
|---|---|---|
| Antigen | FM-1 | FM-2 |
| γ chain peptide 312–324 (FSTWDNDNDKFEG)(SEQ ID NO: 3) | – | – |
| Aα chain (1–625) (a) | – | – |
| Bβ chain (1–461) (a) | – | – |
| γ chain (1–411) (a) | – | – |

In Table 1, the reactivity of each monoclonal antibody was examined by directly coating each antigen on the 96-well ELISA plate. The symbol "+" means that the reaction was observed in ELISA, whereas the symbol "–" means that the reaction was not observed in ELISA. The amino acid sequences of the Aα chain peptide 17–26, the Bβ chain peptide 15–24, and the γ chain peptide 312–324 are shown by the one-letter expression. The above three peptides used are commercially available (Peputido Kenkyujo).
(a): Each antigen was coated on the 96-well ELISA plate, after solubilized with 5M urea.
(b): Each antigen was coated on the 96-well ELISA plate, after solubilized with 50 mM acetate buffer (pH 3.5).

The antigens without the marker (a) or (b) were coated on the 96-well ELISA plate, after dissolved in 0.1M tris-HCl buffer (pH 8.0).

Further, the fibrinogen fragments X, Y, E, Dcate, Degta and D dimer were not reacted with the monoclonal antibody FM-1 or FM-2, even after treated with 5M urea. However, the fibrin fragments X, Y, and E became reactive with the monoclonal antibodies FM-1 and FM-2, after treated with 5M urea. The monoclonal antibodies FM-1 and FM-2 do not react with the 5M urea-treated Aα chain (1-625) of fibrinogen, Aα chain (1-208) of fibrinogen fragment X, or Aα chain (1-78) of fibrinogen fragment E, but react with the 5M urea-treated Aα chain (17-625) of fibrin monomer, Aα chain (17-208) of x monomer, and Aα chain (17-78) of fibrin fragment E.

The above results suggest that the epitope which the above monoclonal antibodies FM-1 and FM-2 recognize exists in the E domain; namely, the epitope exists in the urea-treated E domain where the fibrinopeptide A is or fibrinopeptides A and B are released. More particularly, the results show that the above monoclonal antibodies recognize the Aα chain (17-78) of E domain, namely, the Aα chain (17-78) of E domain where the fibrinopeptide A is or fibrinopeptides A and B are released, and treated with urea.

Example 4

Binding of Antibodies and Insoluble Carrier (Latex)

A solution (2 ml) containing the monoclonal antibody FM-1 (2.0 mg/ml) and a latex solution (2 ml) (2% polystyrene, Dow Chemical Co.: particle size=0.482 μm) were mixed together and stirred for about 1 hour. The mixture was centrifuged (20,000×g, 10 minutes), and then the precipitate was suspended in a 0.1% BSA solution and stirred for about 1 hour. The resulting suspension was again centrifuged (20,000×g, 10 minutes), and then the precipitate was suspended in 0.1M tris-HCl buffer (pH 8.0) and stirred for about 2 hours. Thus, a liquid containing a monoclonal antibody FM-1/latex complex was obtained. In the same manner, monoclonal antibody FM-2 was used to prepare liquid containing complex of a monoclonal antibody FM-21 latex complex.

The complex of the mixture of the monoclonal antibodies with the latex was prepared as follows: 2 ml of aqueous solution containing 0.66 mg/ml of each of the monoclonal antibodies FM-1 and FM-2 was mixed with 2 ml of a latex solution (2% polystyrene, Dow Chemical Co., particle size= 0.482 μm) and the mixture was stirred for about 1 hour. Thereafter, the mixture was treated in the same manner as above to prepare the monoclonal antibody FM-1/ monoclonal antibody FM-2/latex complex.

The same procedure was repeated, except that an aqueous solution containing 1 mg/ml of each of the monoclonal antibody FM-1 and monoclonal antibody FM-2 was mixed in an equal amount of a latex solution, to prepare a monoclonal antibody FM-1/monoclonal antibody FM-2/latex complex.

Example 5

Determination by Agglutination on Slide

The antibody-latex-complex containing solution (40 μl) prepared in Example 4 and aqueous solutions (15 μl) containing various concentrations of urea-solubilized fibrin monomer were mixed on a slide glass and rocked. After 3 minutes, the agglutination was examined visually. The results are shown in Table 2. 0.1M Tris-HCl buffer (pH 8.0) containing 5M urea was used for dilution.

TABLE 2

| Monoclonal antibody/latex complex | Concentration of urea-solubilized fibrin monomer (μg/ml) | | | | | | | |
|---|---|---|---|---|---|---|---|---|
| | 128–256 | 64–128 | 64–32 | 16–32 | 8–16 | 4–8 | 2–4 | 0–2 |
| FM-1 | + | + | + | + | + | + | + | – |
| FM-2 | + | + | + | + | + | + | + | – |
| FM-1 + FM-2 | + | + | + | + | + | + | + | – |
| FM-1/FM-2 | + | + | + | + | + | + | + | – |

In Table 2, "+" means that there is agglutination, while "–" means that there is no agglutination. Further, in the column of the antibody/latex complex in Table 2, the type of the complex is expressed by the monoclonal antibody bonding with the complex. Therefore, for example, FM-1 means a monoclonal antibody FM-1/latex complex, and FM-1+ FM-2 means a mixture of an equal amounts of a monoclonal antibody FM-1/latex complex and a monoclonal antibody FM-2/latex complex. Further, FM-1/FM-2 means a monoclonal antibody FM-1/monoclonal antibody FM-2/latex complex.

Example 6

Recovery Test for Purified FM Added

The concentrations of soluble fibrin in five samples (plasma from healthy person A, healthy person B, DIC patient C, DIC patient D, and DIC patient E) were measured using the monoclonal antibody FM-1/latex complex solution of Example 5. Then, 2 μg/ml, 4 μg/ml, and 16 μg/ml of purified urea-solubilized fibrin monomer were added to the samples and recovery tests were carried out. The measurement values were obtained semiquantitatively from the number of dilutions of the sample eliminating the agglutination. As shown in Table 3, good recovery was observed. Further, 2 μg/ml, 4 μg/ml, and 16 μg/ml of purified acid-solubilized fibrin monomer were added to the samples and recovery tests were carried out to obtain the results similar to those of the above procedure.

TABLE 3

| Sample | Concentration of soluble fibrin (μ/ml) | Amount of urea-solubilized fibrin monomer added (μg/ml) | After addition |
|---|---|---|---|
| A | <2 | 5 | 4–8 |
|   |    | 10 | 8–16 |
|   |    | 20 | 16–32 |
| B | <2 | 5 | 4–8 |
|   |    | 10 | 8–16 |
|   |    | 20 | 16–32 |
| C | 2–4 | 5 | 4–8 |
|   |    | 10 | 8–16 |
|   |    | 20 | 16–32 |
| E | 16–32 | 5 | 16–32 |
|   |    | 10 | 32–64 |
|   |    | 20 | 32–64 |

Example 7

Figure 1:
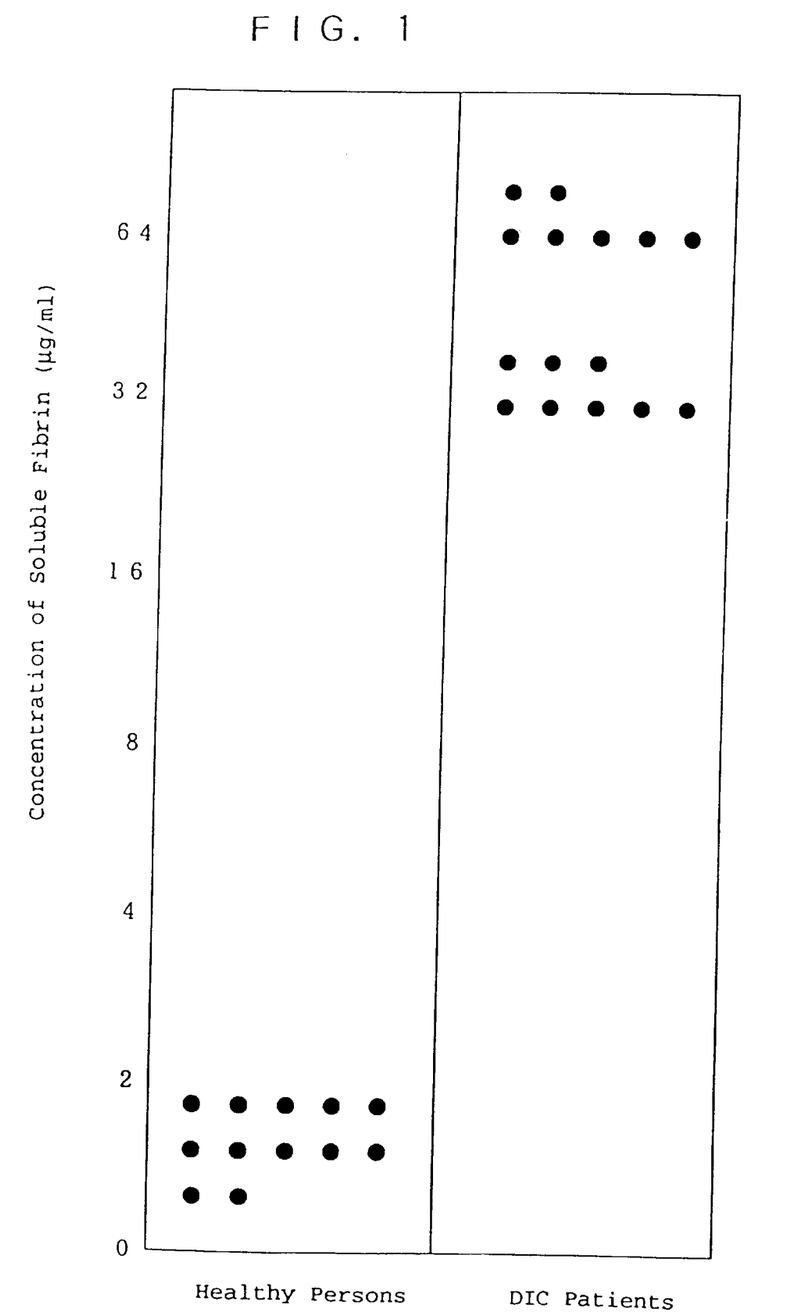
FIG. 1 is a graph illustrating the results of the determination of soluble fibrin in samples from healthy persons or DIC patients as carried out in Example 7.

Concentration of Soluble fibrin in Healthy persons and Patients Suffering from DIC The monoclonal antibody FM-1/latex complex solution used in Example 6 was used to measure the amounts of soluble fibrin of 12 samples of the plasma from healthy persons and 15 samples of the plasma from DIC patients. The results are shown in FIG. 1. The amount of soluble fibrin of the healthy persons was less than 2 μg/ml in all cases. To the contrary, the value for the DIC patients wasover 32 μg/ml in all cases.

Example 8

Assay of Soluble Fibrin by EIA (a) Preparation of insoluble antibody

An antibody liquid was prepared from the monoclonal antibody FM-1 and 50 mM phosphate buffer-physiological saline (ph 7.5) so that the protein concentration in the IgG fraction of the monoclonal antibody FM-1 became 5 μg/ml. The antibody liquid was poured to each well of the 96-well ELISA plate (Immulon; Nippon Dynatech K. K.) in an amount of 50 μl, respectively, and allowed to stand at 4° C. for 24 hours.

(b) Preparation of labeled antibody

The IgG fraction of the monoclonal antibody FM-2 was labeled with horse radish peroxidase (HRP) to obtain the labeled antibody.

(c) Preparation of standard curve

Figure 2:
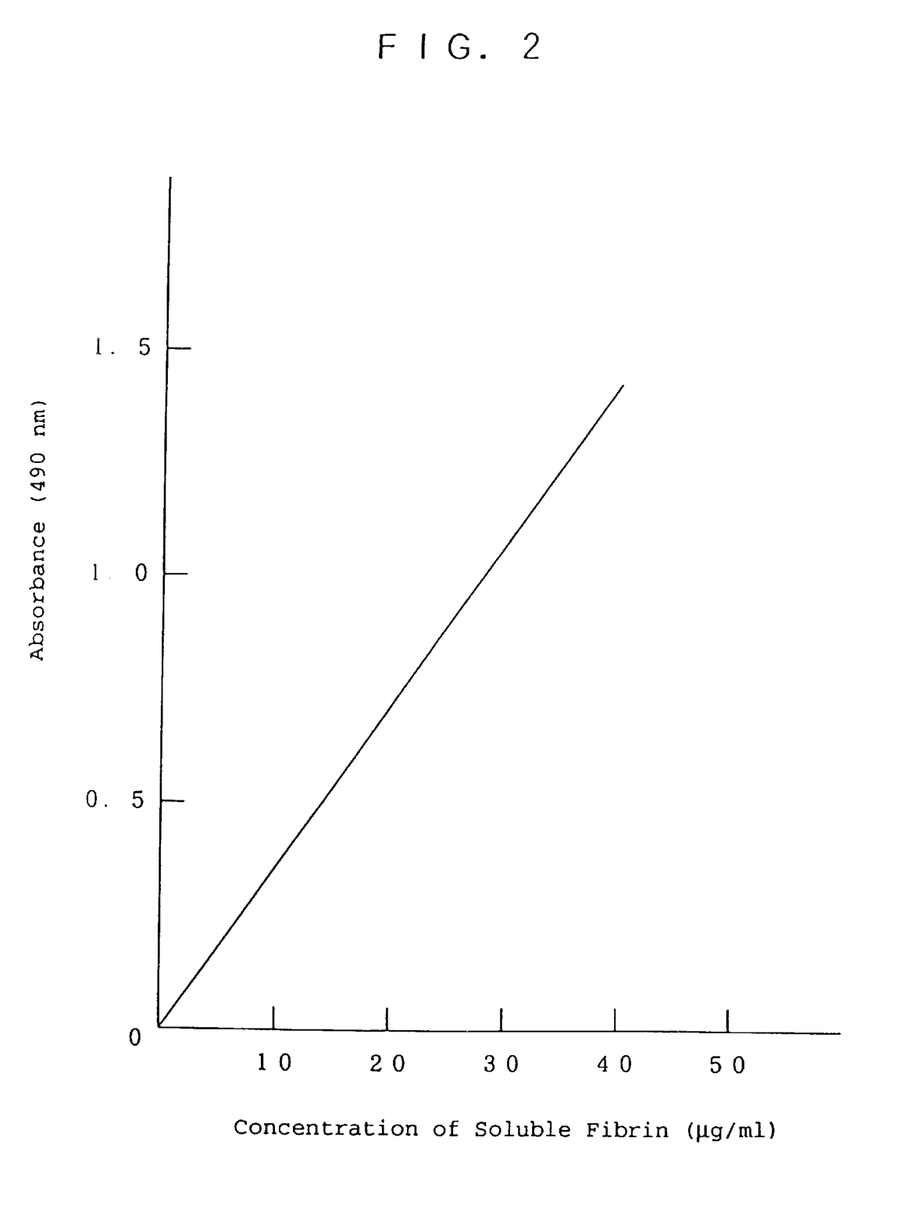
FIG. 2 is a standard curve of EIA as carried out in Example 8.

The 96-well ELISA plate carrying the immobilized monoclonal antibody FM-1 prepared in (a) was washed three times with 0.05% Tween 20-physiological saline. The normal plasma (50 μl) containing 40 μg/ml, 20 μg/ml, 10 μg/ml, 5 μg/ml, 2 μg/ml, 1 μg/ml, or 0.5 μg/ml of the urea-solubilized fibrin monomer obtained in Example 1(a) was poured into the wells, and the reaction was performed at 25° C. for 10 minutes. The plate was washed three times with 0.05% Tween 20-physiological saline. Then, 50 μl of a solution of the monoclonal antibody FM-2 labeled with horse radish peroxidase (HRP) as prepared in (b) in 0.05% Tween 20-physiological saline (pH 7.5) was added to the wells and the reaction was performed at 25° C. for 10 minutes. After the plate was washed three times with 0.05% Tween 20-physiological saline, 200 μl of a HRP substrate solution (50 mM phosphate buffer containing 0.5 mM aminoantipyrine, 10 mM phenol, 0.005% aqueous peroxide; pH 7.5) was added to each well, and the reaction was performed at 25° C. for 10 minutes. The absorption at 490 nm of each well was measured. The resulting standard curve is shown in FIG. 2. When the normal plasma containing 40 μg/ml, 20 μg/ml, 10 μg/ml, 5 μg/ml, 2 μg/ml, 1 μg/ml, or 0.5 μg/ml of the acetate-solubilized fibrin monomer was used, the same results were obtained.

Example 9

Figure 3:
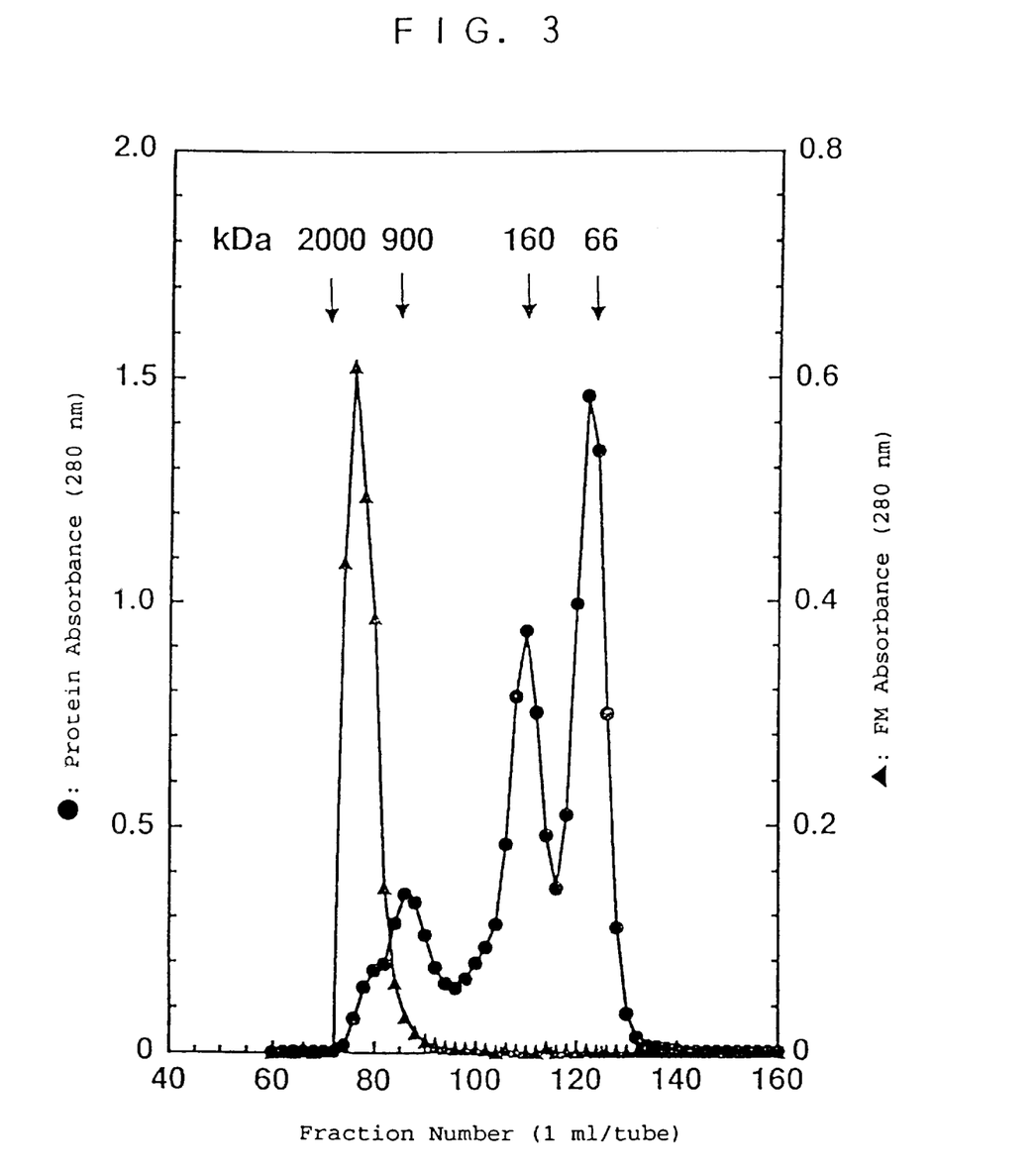
FIG. 3 is a graph illustrating the results of molecular sieve chromatography by Sephacryl S-300 of normal serum to which fibrin monomer solubilized with acetic acid as carried out in Example 9.

Existing Mode and Reactivity of Soluble Fibrin in Normal Plasma to which Acetic Acid-solubilized Fibrin Monomer The acetate-solubilized des AABB fibrin monomer was added to the normal plasma so that the concentration became 200 μg/ml, and the whole was incubated at 37° C. for 30 minutes. The resulting reagent was diluted with 50 mM tris-HCl buffer (pH 8.0) containing 0.15M NaCl to 4 times its volume. The diluted reagent was filled on the column of Sephacryl S-300 (Pharma; Sweden) equilibrated with the same buffer, and treated by molecular sieve chromatography. The protein concentration and soluble fibrin in the eluted fractions were measured. The soluble fibrin was measured in the same way as in Example 8. FIG. 3 illustrates the pattern of the chromatogram and the activity of the soluble fibrin.

Figure 4:
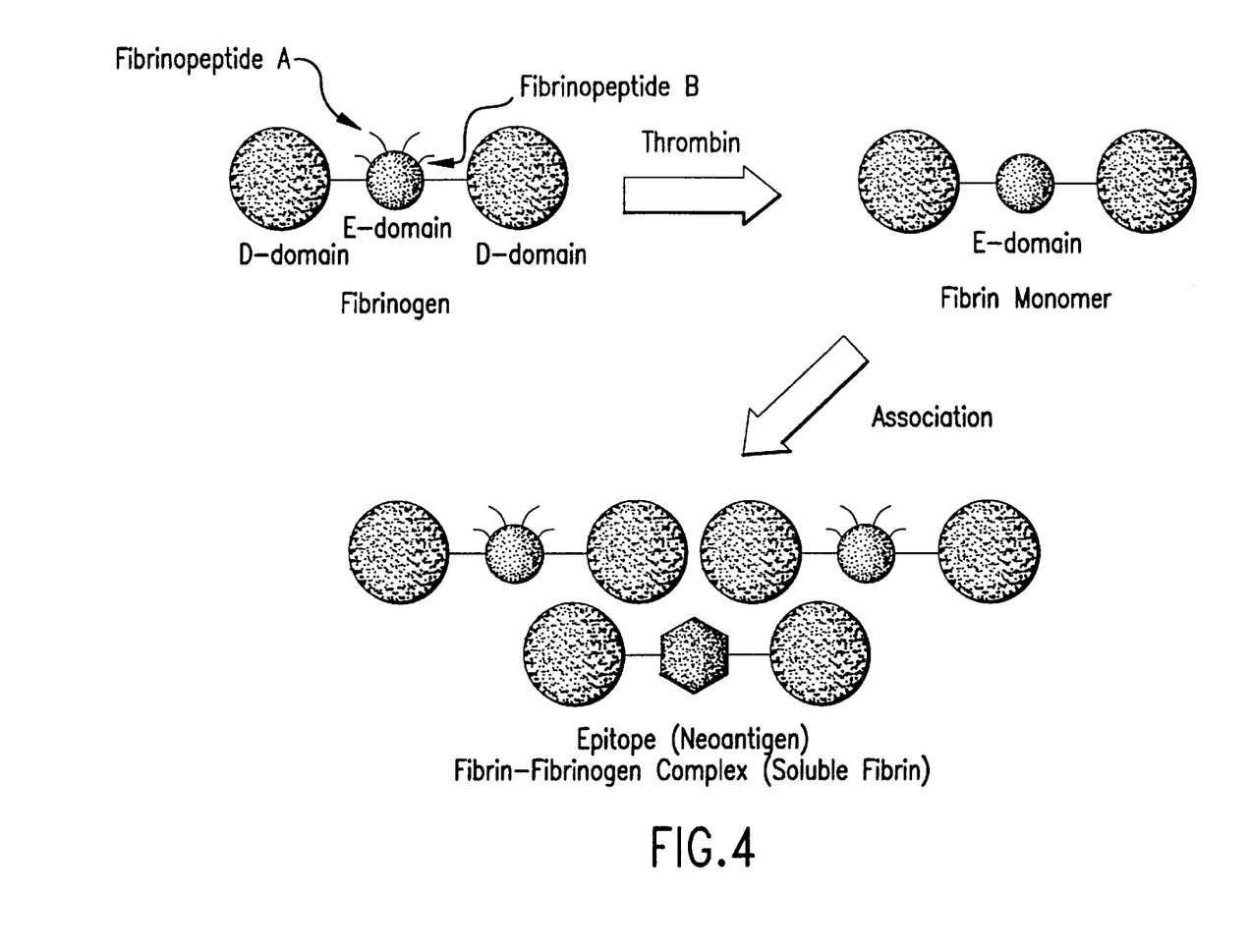
FIG. 4 schematically illustrates an epitope that is newly exposed in an E domain at the time when fibrin monomers are bound with fibrinogens to form a fibrin-fibrinogen complex.

The activity peak of the soluble fibrin is at the molecular weight of between 900,000 and 2,000,000. This means that the acetate-solubilized des AABB fibrin monomer is bound with fibrinogen to form the fibrin-fibrinogen complex. The results in Example 3 show that each of the anti-FM specific monoclonal antibodies FM-1 and FM-2 does not react with the acetate-solubilized fibrin monomer. Further, the results in Example 9 show that when the fibrin-fibrinogen complex is formed by binding the acetate-solubilized fibrin monomer with fibrinogen, the anti-FM specific monoclonal antibodies FM-1 and FM-2 react with the complex. In other words, as schematically shown in FIG. 4, when the acetate-solubilized fibrin monomer (=fibrin monomer in FIG. 4) is bound with fibrinogen to form the fibrin-fibrinogen complex, there is newly exposed an epitope (=neoantigen) which reacts with the anti-FM specific monoclonal antibodies FM-1 and FM-2. The above "fibrin monomer" means a fibrin which is present in the form of a monomer. The fibrin monomer is transiently present in vivo, and may be converted to with an acid in vitro without denatured. These are generally called fibrin monomer.

From the above results, it can be confirmed that the monoclonal antibodies of the present invention react with the neoantigen that newly exposes in a fibrin molecule at the time when a fibrin-fibrinogen complex is formed by binding des AA fibrin or des AABB fibrin and the fibrinogen.

INDUSTRIAL APPLICABILITY

By the monoclonal antibodies of the present invention, it is possible to specifically, readily and rapidly determine the amount of soluble fibrin in the plasma from the patient, even in the form of complex fibrin as bound with fibrinogen, by an agglutination or EIA method, without being affected by fibrinogen, plasmin-degradation products of fibrinogen, the fractions X, Y, D and E, fibrin fragments X, Y, D and E, and plasmin-degradation products of the stabilized fibrin present in plasma, even without pretreating the plasma sample. This is first made possible by the present invention. Accordingly, the present invention provides a useful means for diagnosis and clinical investigation of DIC or the like.

As above, the present invention was explained with reference to particular embodiments, but modifications and improvements obvious to those skilled in the art are included in the scope of the present invention.

not inhibited by a peptide of 17th to 26th amino acids in an amino acid sequence of a fibrinogen Aα chain and a peptide of 15th to 24th amino acids in an amino acid sequence of a fibrinogen Bβ chain.

We claim:

1. A monoclonal antibody which reacts with a neoantigen that is newly exposed in a fibrin molecule at the time when said fibrin molecule complexes with fibrinogen by binding of des AABB fibrin or des AA fibrin with fibrinogen, but does not react with a human fibrinogen.

2. The monoclonal antibody according to claim 1, which specifically reacts with a urea-treated des AABB fibrin, a urea-treated plasmin-degradation product of a stabilized fibrin, and a urea-treated fibrin fragment, but does not react with a urea-treated fibrinogen, a urea-treated plasmin-degradation product of a fibrinogen, a urea-treated des AA fibrin nor a urea-treated des BB fibrin.

3. The monoclonal antibody according to claim 2, wherein a reaction with said urea-treated des AABB fibrin is 4. The monoclonal antibody according to claim 2, wherein a reaction with said urea-treated des AABB fibrin is not inhibited by a peptide of 312nd to 324th amino acids in an amino acid sequence of a fibrinogen γ chain.

5. The monoclonal antibody according to claim 1, which specifically reacts with a urea-treated des AA fibrin, a urea-treated des AABB fibrin, a urea-treated plasmin-degradation product of a stabilized fibrin, and a urea-treated fibrin fragment, but does not react with a urea-treated fibrinogen, a urea-treated plasmin-degradation product of a fibrinogen, nor a urea-treated des BB fibrin.

6. A monoclonal antibody according to claim 5, wherein a reaction with said urea-treated des AA fibrin and said urea-treated des AABB fibrin is not inhibited by a peptide of 17th to 26th amino acids in an amino acid sequence of a fibrinogen Aα chain and a peptide of 15th to 24th amino acids in an amino acid sequence of a fibrinogen Bβ chain.

7. The monoclonal antibody according to claim 5, wherein a reaction with said urea-treated des AA fibrin and said urea-treated des AABB fibrin is not inhibited by a peptide of 312nd to 324th amino acids in an amino acid sequence of a fibrinogen γ chain.

8. A hybridoma characterized by secreting the monoclonal antibody according to claim 1.

9. A method of assaying a human soluble fibrin, characterized by bringing a sample into contact with a monoclonal antibody according to claim 1 immobilized on an insoluble carrier, and observing agglutination.

10. The method according to claim 9 wherein at least one of said monoclonal antibodies is an antibody which specifically reacts with urea-treated des AABB fibrin, a urea-treated plasmin-degradation product of stabilized fibrin and a urea-treated fibrin fragment, but does not react with urea-treated fibrinogen, a urea-treated plasmin-degradation product of fibrinogen, urea-treated des AA fibrin or urea-treated des BB fibrin or is an antibody which specifically reacts with urea-treated des AA fibrin, urea-treated des AABB fibrin, a urea-treated plasmin-degradation product of stabilized fibrin and a urea-treated fibrin fragment but does not react with urea-treated fibrinogen, a urea-treated plasmin-degradation product of fibrinogen or urea-treated des BB fibrin.

11. A method of immunological assaying a human soluble fibrin characterized in that a monoclonal antibody according to claim 1 is immobilized on an insoluble carrier as a first antibody, bringing a sample into contact with said first antibody and then with a labeled second antibody according to claim 1, and detecting a signal from said label of said second antibody bound with an immobilized first antibody which specifically binds human soluble fibrin, or said second antibody unbound from the immobilized first antibody which specifically binds human soluble fibrin, wherein said first and said second antibodies bind to the same epitope or to different epitopes.

12. The method according to claim 11, wherein said first monoclonal antibody and said second monoclonal antibody bind to different epitopes.

13. A method for diagnosing disseminated intravascular coagulation comprising detecting a soluble fibrin in a biological sample by a method according to any one of claims 9 to 12.

* * * * *

UNITED STATES PATENT AND TRADEMARK OFFICE
CERTIFICATE OF CORRECTION

PATENT NO. : 5,821,068
DATED : Oct. 13, 1998
INVENTOR(S) : Gilbu Soe, et al

It is certified that error appears in the above-identified patent and that said Letters Patent is hereby corrected as shown below:

At column 14, line 51, change "newly exposes" to --is newly exposed--.

At column 16, claim 6, line 1 of the claim, change "A" to --The--.

Signed and Sealed this

Twenty-fourth Day of April, 2001

Attest:

NICHOLAS P. GODICI

Attesting Officer

Acting Director of the United States Patent and Trademark Office

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:1:

```
Gly His Arg Pro Leu Asp Lys Lys Arg Glu
1               5                   10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:2:

```
Gly Pro Arg Val Val Glu Arg His Gln Ser
1               5                   10
```

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:3:

```
Phe Ser Thr Trp Asp Asn Asp Asn Asp Lys Phe Glu Gly
1               5                   10
```